United States Patent [19]

Zengel et al.

[11] Patent Number: 4,457,871
[45] Date of Patent: Jul. 3, 1984

[54] PREPARATION OF TRANS CYCLOHEXANE,1,4-DIISOCYANATE AND RELATED COMPOUNDS

[75] Inventors: Hans Zengel, Kleinwallstadt; Manfred Bergfeld, Erlenbach, both of Fed. Rep. of Germany

[73] Assignee: Akzona Incorporated, Asheville, N.C.

[21] Appl. No.: 420,185

[22] Filed: Sep. 20, 1982

Related U.S. Application Data

[62] Division of Ser. No. 215,415, Dec. 11, 1980, Pat. No. 4,418,211, which is a division of Ser. No. 049,112, Jun. 18, 1979, Pat. No. 4,275,223, which is a division of Ser. No. 883,949, Mar. 6, 1978, Pat. No. 4,203,916.

[30] Foreign Application Priority Data

Mar. 11, 1972 [DE] Fed. Rep. of Germany ..... 27105959

[51] Int. Cl.$^3$ ................. C07C 118/00; C07C 119/045
[52] U.S. Cl. ............................ 260/453 P; 260/453 A
[58] Field of Search ........................ 260/453 P, 453 A

[56] References Cited

U.S. PATENT DOCUMENTS 2,728,787 12/1955 Hurwitz et al. ................. 260/453 P
2,773,086 12/1956 Slocombe et al. .............. 260/453 P
3,644,459  2/1972 Cross ............................... 260/453 P Primary Examiner—Dolph H. Torrence
Attorney, Agent, or Firm—Francis W. Young; Robert F. Green

[57] ABSTRACT

A process is disclosed for selectively making trans-cyclohexane-1,4-diisocyanate, trans-cyclohexane-1,4-diamine, a trans-cyclohexane-1,4-diurethane, a trans-cyclohexane-1,4-diurea and trans-cyclohexane-1,4-disulphonyl urea by reacting ammonia with a mixture of cis and trans cyclohexane-1,4-dicarboxylic acid, a lower alkyl ester, a glycol ester, an oligomeric ester or a polyester to make a solid trans-dicarboxylic acid diamide in a first step. The diamide is chlorinated to form trans-cyclohexane-1,4-dicarboxylic acid-bis-N-chloramide. The latter compound is then converted into a (a) trans-cyclohexane-1,4-diamine with an alkali metal hydroxide or alkaline earth metal hydroxide; or into a (b) a trans-cyclohexane-1,4-diurethane by reaction with an alcohol or glycol in a reaction mixture containing an alkali metal hydroxide or alkaline earth metal hydroxide; or into (c) a trans-cyclohexane-1,4-diurea by reaction with a primary or secondary amine in a reaction mixture containing an alkali metal hydroxide or alkaline earth metal hydroxide; or into a (d) trans-cyclohexane-1,4-sulphonyl urea by reaction with a primary sulphonamide in a reaction mixture containing an alkali metal hydroxide and dimethyl formamide and water. The diurea prepared in (c) may be converted into trans-cyclohexane-1,4-diisocyanate with gaseous hydrogen chloride in an inert solvent. The diurethane prepared in (b) and the disulphonyl urea prepared in (d) may be thermally decomposed into trans-cyclohexane-1,4-diisocyanate.

1 Claim, No Drawings

PREPARATION OF TRANS CYCLOHEXANE,1,4-DIISOCYANATE AND RELATED COMPOUNDS

This is a division, of application Ser. No. 215,415, filed Dec. 11, 1980, U.S. Pat. No. 4,418,211, which is a Division of application Ser. No. 049,112, filed June 18, 1979, U.S. Pat. No. 4,275,223 which in turn is a Division of Ser. No. 883,949, filed Mar. 6, 1978 U.S. Pat. No. 4,203,916.

This invention relates to the stereo-specific synthesis of trans-cyclohexane-1,4-diisocyanate, trans-cyclohexane-1,4-diamine, trans-cyclohexane-1,4-diurethanes, trans-cyclohexane-1,4-diureas and trans-cyclohexane-1,4-disulphonyl ureas.

Cyclohexane-1,4-diisocyanate, cyclohexane-1,4-diamine, cyclohexane-1,4-diurethanes, cyclohexane-1,4-disulphonyl ureas and cyclohexane-1,4-diureas are valuable starting materials for the production of polyurethanes, polyamides and other polymers. Important properties of these polymers, e.g. their mechanical strength, shrink resistance and glass transition point, depend particularly upon the stereo isomeric form of the cyclohexane derivatives used. The higher the proportion of trans-isomers in the mixture of the isomeric cyclohexane-1,4-derivatives, the more favorable are these properties. Since any of the heretofore available methods of synthesizing cyclohexane-1,4-derivatives always gives rise to a mixture of the cis- and the trans-isomers, it is desirable to increase the concentration of trans-compound or even to obtain pure trans-isomer.

The starting point in all previous attempts was cyclohexane-1,4-diamine. This compound is one of several produced when p-phenylene diamine is hydrogenated on nickel or cobalt catalysts in methylcyclohexane or in dioxane or decaline at 180° C./100 or 150 atmospheres (Hoshino, Bull. chem. Soc. Japan 19, (1944), 153, 154; J. chem. Soc. Japan 62 (1941), 190, 192; C.A. 1942; 5140; U.S. Pat. No. 2,175,003). In the process described in U.S. Pat. No. 3,520,928, p-phenylene diamine is used in the form of a salt of a mineral acid and hydrogenation is carried out using an acid resistant catalyst, e.g. a platinum or palladium catalyst in aqueous solution at a temperature of from 50° to 150° C. and at pressures of from 0.35 to 14 atmospheres. Ruthenium catalysts are also suitable for the hydrogenation of p-phenylene diamine (Chemical Abstracts Vol. 63 (1965), 11415 h; Vol. 69 (1968), 25775 and Vol. 72 (1970), 132 192k). Alkali-modified ruthenium carrier catalysts are used in the process according to U.S. Pat. No. 3,636,108 (see also Canadian Pat. No. 839,281 and Canadian Pat. No. 892,636) and a catalyst obtained by precipitation of an oxide hydrate of ruthenium is used in the process described in German Offenlegungsschrift No. 2,132,547. The diamino, 1,4-diamino cyclohexane is obtained when 4-nitro aniline is hydrogenated in the presence of colloidal platinum in acetic acid and hydrochloric acid at a temperature of 65° C. (Skita, Borendt, Ber. 52, 1534) or in the presence of a ruthenium catalyst at 20° to 250° C. and a pressure above 7 atmospheres (U.S. Pat. No. 2,606,925). In all of these processes, a mixture of the cis- and the trans-forms is obtained, in which the equilibrium is established at approximately 70% of the trans-form and 30% of the cis-form (Chem. Abstracts 82 (1975), 111 479a).

Trans-cyclohexane-1,4-diamine can be obtained from this isomeric mixture by fractional crystallization as described in U.S. Pat. No. 3,657,345, but several crystallizations are required to achieve this. More efficient separation of the isomers is possible by fractional crystallization of suitable derivatives. One example of this is the fractional crystallization of bis-methyl carbamates followed by hydrolysis with hydrogen chloride (Chem. Abstr. 74 (1971), 87370c). One disadvantage of this method is that it requires an additional step for the preparation of the derivative and another for regenerating the diamine.

In U.S. Pat. No. 3,491,149 a process is described in which the isomeric mixture is reacted with an organic polyhydroxyl compound having from 2 to 13 carbon atoms and 2 to 4 hydroxyl groups, optionally in the presence of a solvent such as cyclohexane dimethanol, to produce a "polyolate" coordination compound. The cis- and trans-isomers of this coordination compound differ more widely from each other in their crystallization behavior than the corresponding 1,4-diamino cyclohexane isomers and can therefore be separated from each other more easily. The trans-coordination compound is subsequently subjected to fractional or azeotropic distillation at atmospheric or reduced pressure so that trans-1,4-diamino cyclohexane and the polyhydroxyl compound are again separated from each other. Alternatively, however, this process can be carried out with only a single crystallization step, in which case only part of the original trans-isomer is recovered. The filtrate then contains the remainder of the trans-isomer and virtually all of the original cis-isomer.

Such mixtures of stereo isomers of 1,4-diamino cyclohexane which contain more cis-isomer than corresponds to the equilibrium concentration may be worked up by a process described in U.S. Pat. No. 3,657,345. In this process, the reaction mixture is treated with hydrogen under pressure at 150° to 300° C. in the presence of an alkali-modified ruthenium catalyst and in the presence of ammonia. The usual equilibrium of about 70% trans-isomer and about 30% cis-isomer is re-established and part of the trans-isomer may again be separated from the cis-isomer by fractional crystallization. The process may also be carried out with the addition of p-phenylene diamine.

The trans-isomer can also be obtained in a comparatively pure form by converting a pure precursor of the trans-isomer into trans-1,4-diamino cyclohexane. The following are examples: reaction of finely divided trans-hexahydroterephthalic acid diazide with water followed by treatment with water under pressure at 120° C. and heating of the reaction product to 140° C. with concentrated hydrochloric acid under pressure (Curtius, J. prakt. Chem. (2) 91, 33); heating of trans-hexahydro-p-phenylene diurethane with concentrated hydrochloric acid in a tube reactor (Curtius, J. prakt. Chem. (2) 91, 34); hydrogenation of trans-1,4-dinitro-cyclohexane in acetic acid and in the presence of a platinum catalyst at 25° C. (A. T. Nielsen, J. Org. Chem. Vol. 27 (1962), 1,998–2,001). In these processes, however, the problem of preparing a stereo specific isomer is simply shifted to the chemical precursor stage of the isomer.

Pure trans-cyclohexane-1,4-diamine obtainable by the methods described above may subsequently be converted into trans-cyclohexane-1,4-diisocyanate by phosgenation in known manner, and this diisocyanate may in turn be converted into pure trans-cyclohexane-1,4-diurethanes or -diureas. Summarizing, it has been found that none of the processes mentioned above is a stereo specific synthesis of the cyclohexane-1,4-derivatives but that they require the separation of a mixture of cis- and trans-isomers of cyclohexane-1,4-diamine or of a precursor thereof and secondary reactions of the separated trans-isomer.

Theoretically, Hofmann's degradation of cyclohexane-1,4-dicarboxylic acid diamide is available for the preparation of cyclohexane-1,4-diamine. As is well known, Hofmann's degradation of carboxylic acid amides leads to the amine via the stages of the N-chloramide and the isocyanate. If the reaction is carried out in the presence of sodium alcoholate in an alcohol, a urethane is obtained; if the reaction is carried out in the presence of a primary or secondary amine, a substituted urea is obtained; if the reaction is carried out in the presence of a primary sulphonamide in a mixture of dimethylformamide and water, a substituted sulphonyl urea is obtained. The N-chloramide, and hence the isocyanate, can only rarely be isolated as intermediate products of Hofmann's degradation. It is therefore generally necessary to synthesize the isocyanate from the substituted urea, a urethane or a sulphonyl urea or by some other means. Hofmann's degradation of cyclohexane-1,4-dicarboxylic acid diamide also leads directly to cyclohexane-1,4-diamine; the intermediate stages cannot be isolated. The cyclohexane-1,4-dicarboxylic acid diamide required for this process can easily be obtained in an analytically pure form, either by the process described in German Pat. No. 2,410,537, which consists of reacting cyclohexane-1,4-dicarboxylic acid with urea in oleum having a concentration of at least 10% by weight or in chlorosulphonic acid, and which gives a yield of 82%, or by the process disclosed in German Offenlegungsschrift No. 2,437,470, which consists of ammonolysis of an oligoester or polyester of cyclohexane-1,4-dicarboxylic acid, and which provides a yield of 97%. If a product obtained by one of these processes or by any of the other known processes, for example from the ammonium salt of carboxylic acid or by the reaction of the anhydride, the acid chloride or an ester of cyclohexane-1,4-dicarboxylic acid is subjected to Hofmann's degradation, the product obtained is invariably a mixture of the cis-and trans-isomers. This is also true when cyclohexane-1,4-dicarboxylic acid-bis-N-chloramide obtained by the chlorination of cyclohexane-1,4-dicarboxylic acid diamide according to the process described in German Offenlegungsschrift No. 2,502,412 is subjected to Hofmann's degradation. In other words, it has hitherto been impossible to prepare any of the above mentioned pure trans-isomers by means of Hofmann's degradation.

It is therefore an object of this invention to provide a process for selectively making trans-cyclohexane-1,4-diisocyanate, trans-cyclohexane-1,4-diamine, trans-cyclohexane-1,4-diurethane, trans-cyclohexane-1,4-diurea, and trans-cyclohexane-1,4-sulphonyl urea which does not require separation of the trans- and cis-isomers.

Another object of the invention is to provide a process for preferentially making one of the said trans-compounds from a mixture of cis- and trans-isomers of the starting compound.

It has now surprisingly been found that with suitable choice of the reaction parameters it is possible to provide a method of synthesis by which the desired trans-isomer can be obtained stereo-specifically and in high yields from a cis/trans mixture of cyclohexane-1,4-dicarboxylic acid or one of its monomeric, oligomeric or polymeric esters.

The present invention therefore provides a process for the preparation of trans-cyclohexane-1,4-diisocyanate, trans-cyclohexane-1,4-diamine, trans-cyclohexane-1,4-diurethanes, trans-cyclohexane-1,4-diureas or trans-cyclohexane-1,4-disulphonyl-ureas which is characterized in that cyclohexane-1,4-dicarboxylic acid, a lower alkyl ester, a glycol ester, an oligomeric ester or a polyester thereof or a mixture of the aforesaid compounds is used as starting material, the said acid or ester (or esters) is treated with ammonia in a polyhydric alcohol such as ethylene glycol at a temperature of from about 25° to about 200° C. and under an ammonia partial pressure of 0.1 to 50 bar, and the solid dicarboxylic acid diamide which separates under these conditions is freed from water soluble constituents adhering to it and is suspended in aqueous mineral acid or in water and chlorinated at temperatures of from 0° to 40° C., and the cyclohexane-1,4-dicarboxylic acid-bis-N-chloramide thereby obtained is washed free from chlorine with cold water and finally (a) is converted into trans-cyclohexane-1,4-diamine by treatment with an alkali metal or alkaline earth metal hydroxide, (b) is converted into a trans-cyclohexane-1,4-diurethane by reaction with an alcohol or with a glycol in a reaction mixture containing an alkali metal hydroxide or alkaline earth metal hydroxide or an alcoholate, (c) is converted into a trans-cyclohexane-1,4-diurea by reaction with a primary or secondary amine in the presence of an alkali metal or alkaline earth metal hydroxide or (d) is converted into a trans-cyclohexane-1,4-sulphonyl urea by treatment with a primary sulphonamide in the presence of an alkali metal hydroxide in a mixture of dimethyl formamide and water or the diurea obtained according to (c) is converted into trans-cyclohexane-1,4-diisocyanate by treatment with gaseous hydrogen chloride in an inert solvent or the urethane obtained according to (b) is converted into trans-cyclohexane-1,4-diisocyanate by thermal decomposition in the gaseous phase or in the liquid phase, optionally in an inert solvent or the disulphonyl urea obtained according to (d) is converted into trans-cyclohexane-1,4-diisocyanate by heat treatment in an inert solvent.

In the process provided by the present invention, the ratio of cis- to trans-isomer in the starting material is unimportant since the desired reaction products are obtained substantially exclusively in the trans-form even if the starting materials have a very high cis/trans ratio, for example of 10:1. It is known that in compounds which exist in the stereo isomeric form, an equilibrium between the cis-form and the trans-form is invariably established under strongly alkaline conditions and at high temperatures. It is therefore surprising that the process according to the invention, in which strongly alkaline conditions and high reaction temperatures are employed in at least two reaction stages, nevertheless results almost exclusively in trans-compounds, which means that in the present case the establishment of a cis/trans equilibrium unexpectedly does not take place.

One important feature of the process provided by the invention is that it cannot be carried out with any cyclohexane-1,4-dicarboxylic acid diamide prepared by just any available method. On the contrary, the cyclohexane-1,4-dicarboxylic acid diamide used as the starting material must be one which has been prepared by ammonolysis of a lower alkyl or glycol ester or of an oligomeric or polymeric ester of cyclohexane 1,4-dicarboxylic acid in a polyhydric alcohol or by amidation of cyclohexane-1,4-dicarboxylic acid in the presence of a polyhydric alcohol, and only the water insoluble constituents may be used for the subsequent reaction.

A process for the preparation of cyclohexane-1,4-dicarboxylic acid diamide from oligomeric or polymeric esters of cyclohexane-1,4-dicarboxylic acid is disclosed in German Pat. No. 2,437,470. Examples of polyhydric alcohols from which the required oligo esters or polyesters may be obtained include ethylene glycol, diethylene glycol, 1,3-propane diol, 1,4-butane diol, 1,6-hexane diol 1,8-octane diol, 1,10-decane diol, 1,2-propane diol, 2,2-dimethyl-1-1,3-propane diol, 2,2,4-trimethyl hexane diol, cyclohexane-1,4-dimethanol, glycerol and the like. Copolycondensates of cyclohexane-1,4-dicarboxylic acid with several of the above mentioned diols may also be used as starting materials. The polyhydric alcohols already mentioned above as ester components, or mixtures of these alcohols, may be used as the reaction medium. It is preferred to use, as the reaction medium, that alcohol which forms the alcohol component of the cyclohexane-1,4-oligoester or -polyester. According to a preferred embodiment of the invention, an oligomeric or polymeric ethylene glycol ester of cyclohexane-1,4-dicarboxylic acid is used as the starting material, and ammonolysis is carried out in ethylene glycol. Moreover, instead of using a previously prepared oligoester or polyester, the reaction mixture obtained from its preparation, which contains excess diol, may be used. The quantities of polyhydric alcohol used as reaction medium are in the region of 100% to 1,000% by weight, based on the quantity of oligoester or polyester used.

The reaction temperatures may be within the range of from 25° to 200° C. and are preferably from about 50° to about 160° C. The ammonia partial pressures are in the region of 0.1 to 50 bar. For practical and economic reasons, ammonolysis is preferably carried out at ammonia partial pressures below 20 bar. The reaction time required depends on the oligoester or polyester put into the process, the ammonia partial pressure and the reaction temperature and, where ammonolysis is carried out on an oligoester or polyester suspension, it also depends decisively on the thickness of the starting material. If ammonolysis is carried out in solution or on a very finely divided material, it is generally completed in less than two hours under the preferred conditions of the process. Longer reaction times are required for a material consisting of very coarse particles, for example from five to six hours in the case of a polyester with a particle size of 5 mm.

Ammonolysis may be carried out, for example, by first dissolving or suspending the oligoester or polyester in the polyhydric alcohol and then passing gaseous ammonia through the solution or suspension under the reaction conditions, at the same time thoroughly mixing the components. The solution or suspension may also be introduced into an autoclave into which the required quantity of ammonia is introduced into gas space while the contents of the autoclave are vigorously mixed.

When a very coarse polymer material is used, it is advisable first to dissolve it in the polyhydric alcohol at a temperature above the intended reaction temperature and then to cool the solution to the reaction temperature. Under these conditions, the polyester precipitates in a finely divided form if it does not remain completely in solution, and thus becomes more readily accessible to the action of ammonia. In this way, short reaction times can be achieved for even a coarse starting material.

The diamide may be prepared from a glycol ester by the process described in U.S. Pat. No. 3,296,303. According to the process described in this U.S. patent, ammonolysis is carried out on an ester of ethylene glycol, propylene glycol or diethylene glycol at a temperature of from 25° C. to 130° C. in excess glycol, but the process is not restricted to the starting compounds and temperature conditions mentioned in the Patent. Other suitable glycol esters are those mentioned above as starting compounds for the preparation of oligomeric and polymeric esters.

Lower alkyl esters may be converted similarly into cyclohexane-1,4-dicarboxylic acid diamide. Suitable lower alkyl esters include in particular compounds having from 1 to 4 carbon atoms in the alkyl group, for example methyl, ethyl, propyl, butyl, and isobutyl esters of cyclohexane-1,4-dicarboxylic acid. It is advantageous to trans-esterify the alkyl ester in a polyhydric alcohol, preferably in ethylene glycol, and to remove the resulting lower alcohol from the reaction mixture by distillation. This process may be carried out by heating the alkyl ester in the polyhydric alcohol at a temperature of from 50° C. to 120° C. while passing a slow stream of ammonia through the reaction mixture. It is surprisingly found that trans-esterification is so greatly accelerated by gaseous ammonia that the usual trans-esterification catalyst can be dispensed with. Subsequent ammonolysis of the glycol ester results in a purer diamide and higher yields than ammonolysis of the alkyl ester because the lower alcohols which are split off during ammonlysis form by-products with ammonia, e.g. primary amines.

Ammonolysis of polymeric, oligomeric and monomeric diesters of cyclohexane-1,4-dicarboxylic acid may be carried out, by the process described in German Pat. No. 2,437,470, at temperatures of from 25° C. to 200° C., preferably at 50° C. to 160° C., and at an ammonia partial pressure of from 0.1 to 50 bar, preferably at 1 to 20 bar.

Cis/trans-cyclohexane-1,4-dicarboxylic acid may also be converted into cyclohexane-1,4-dicarboxylic acid diamide by reaction with ammonia in a polyhydric alcohol. This reaction is suitably carried out by esterifying the cis/trans mixture of cyclohexane-1,4-dicarboxylic acid with a polyhydric alcohol, preferably ethylene glycol, and then introducing ammonia into the reaction mixture under the above mentioned conditions of ammonolysis at 50° C. to 160° C. and an ammonia partial pressure of from 0.1 to 50 bar. The yield of cyclohexane-1,4-dicarboxylic acid diamide obtained in this process is about 84% of the theoretical yield.

Essential to the process according to the invention is not only the particular method of synthesis to be used for the required cyclohexane-1,4-dicarboxylic acid diamide but also the feature that only that portion of the dicarboxylic acid diamide which is obtained as solid from the reaction mixture of the special process of preparation may be used as starting compound for the subsequent stages of synthesis, and only after it has been freed from the water-soluble constituents adhering to it. In the course of the preparation of the cyclohexane-1,4-diamide in a polyhydric alcohol, a substantial proportion of the diamide is left dissolved in the reaction mixture. When ethylene glycol is used as the reaction medium, only about 80% of the diamide, which is formed in virtually quantitative yield, is finely obtained. The diamide which remains dissolved in the filtrate of the reaction mixture after removal of the solid diamide is not suitable for the synthesis of the pure trans-compound to be obtained according to the invention. The same applies to the water-soluble or methanol-soluble diamide constituents which adhere to the solid precipitated diamide. They must be removed by washing, for example with water. However, the proportions of diamide which are dissolved in the reaction mixture are not lost. The glycollic mother liquor may be used again for ammonolysis, in other words it may be recycled. In that case, it is even found that the proportion of cyclohexane-1,4-dicarboxylic acid diamide precipitated from the reaction mixture is increased to over 95% of the theoretical yield. The mother liquor left after removal of the solid precipitated dicarboxylic acid diamide is therefore kept in circulation in the process according to the invention, i.e. it is re-used for the reaction of the cyclohexane-1,4-dicarboxylic acid or its esters. The water soluble diamide fraction contained in the wash waters of the precipitated solid diamide may also be used again for ammonolysis. The wash waters may be collected, concentrated by evaporation, combined with the glycollic mother liquor and then freed from water and any adhering lower alcohols by distillation.

Cyclohexane-1,4-dicarboxylic acid diamido obtained by the process described above is then suspended in an aqueous mineral acid by the process according to German Offenlegungsschrift No. 2,502,412 or chlorinated in water at 0° to 40° C. to form cyclohexane-1,4-dicarboxylic acid-bis-N-chloramide.

Any suitable aqueous mineral acid may be used such as, for example, dilute aqueous hydrochloric acid, sulphuric acid or phosphoric acid. It is preferred to start with a neutral aqueous suspension of the diamide so that the hydrogen chloride formed as by-product of chlorination dissolves in the reaction mixture and the reaction therefore takes place in a dilute aqueous hydrochloric acid medium. Moreover, it is preferred to start with a dilute hydrochloric acid or dilute sulphuric acid aqueous suspension of the diamide.

Chlorination of the diamide is exothermic. It may be carried out at a temperature of from 0° C. to 40° C. Higher temperatures are a disadvantage in that they cause the formation of substantial quantities of cyclohexane-1,4-dicarboxylic acid due to hydrolysis. For economic reasons, chlorination is preferably carried out at 5° C. to 25° C., and the heat of reaction may be removed by cooling with water.

Chlorination may be carried out either at atmospheric pressure or at an elevated pressure. Although the reaction time required decreases with increasing pressure, the preferred pressure range is approximately between 1 and 6 bar for economic reasons.

Since chlorination takes place in a heterogeneous phase, thorough mixing of the suspension is required. The reaction mixture should at least be diluted sufficiently to allow it to be easily stirred or mixed in some other way. The preferred dilution of the reaction mixture is about 100 to 200 g of diamide per liter of water or aqueous mineral acid.

When the above reaction conditions are observed, chlorination is completed after about 0.25 to 2 hours. The diamide is converted virtually quantitatively into the bis-N-chloramide without any solution taking place in the meantime. The only solid contained in the suspension after chlorination has been completed is cyclohexane-1,4-dicarboxylic acid-bis-N-chloramide, which can be separated easily from the liquid phase e.g. by filtration or centrifuging. Water at 0° C. to 15° C. is used for washing, preferably ice water. The precipitate should be washed free from chlorine because the presence of free chlorine acting as oxidizing agent interferes with the subsequent Hofmann reaction. The product is obtained maximally pure after washing followed by drying, e.g. at 50° C. under vacuum. For the subsequent stages of the reaction, only the insoluble portions of cyclohexane-1,4-dicarboxylic acid-bis-N-chloramide which have been washed free from chlorine with cold water are used.

The cyclohexane-1,4-dicarboxylic acid-bis-N-chloramide which has been obtained as described above by ammonolysis of a monomeric, oligomeric or polymeric ester of cyclohexane-1,4-dicarboxylic acid in a polyhydric alcohol or by amidation of cyclohexane-1,4-dicarboxylic acid in a polyhydric alcohol followed by chlorination of the resulting cyclohexane-1,4-dicarboxylic acid diamide may be subsequently converted into a diamine, a diisocyanate, a diurethane, a diurea or a disulphonylurea.

Synthesis of the trans-cyclohexane-1,4-diamine is carried out by reaction of cyclohexane-1,4-dicarboxylic acid-bis-N-chloramide with an alkali metal or alkaline earth metal hydroxide. This is carried out by dissolving or suspending the bis-N-chloramide in a hydroxide, preferbly an aqueous hydroxide, and heating. Any alkali metal or alkaline earth metal hydroxide may be used but sodium hydroxide and calcium hydroxide are preferred to the other hydroxides such as potassium hydroxide, barium hydroxide, magnesium hydroxide and the like for economic reasons. The hydroxide is preferably used in a stochiometric quantity. It is neither necessary nor of advantage to use an excess of hydroxide.

The reaction of the bis-N-chloramide is preferably carried out at a temperature within the range of from about 20° C. to about 95° C., preferably from about 30° C. to 80° C. Solutions or suspensions of bis-N-chloramide at concentrations of from 5% to 45% by weight are preferably used.

The diamine may be isolated from the reaction mixture by extraction with chloroform, 1,2-dichloroethane or some other solvent. However, the diamine precipitates in such purity from the reaction mixture that it may also be separated by fractional crystallization. Separation by steam distillation or precipitation of the amine as a salt with sulphuric acid or hydrochloric acid are other possible methods of separation.

The rearrangement reaction is highly exothermic and is preferably carried out adiabatically. If an adiabatic method is impossible due to excessive evolution of heat, as may happen if high initial concentrations of cyclohexane-1,4-dicarboxylic acid-bis-N-chloramide are employed, the reaction may be carried out under conditions of vapor cooling, for example using methylene chloride as vaporizing agent.

To pressure trans-cyclohexane-1,4-diurethanes, cyclohexane-1,4-dicarboxylic acid-bis-N-chloramide is reacted with a hydroxyl compound in the presence of an alkali metal or alkaline earth metal hydroxide. The hydroxyl compounds used may be any alcohol or phenol which is capable of at least partly dissolving an alkali metal or alkaline earth metal hydroxide. Such hydroxyl compounds include monohydric alcohols, in particular the lower alkyl alcohols such as methyl, ethyl, propyl, isopropyl, butyl and isobutyl alcohol as well as glycols, e.g. ethylene glycol, propylene glycol and glycerol, and many carbocyclic and heterocyclic phenols.

The following are examples of suitable carbocyclic phenols: monovalent monocyclic phenols such as phenol itself, o-, m- and p-cresol, the xylenols, thymol and carvacrol, divalent and higher valent monocyclic phenols, e.g. pyrocatechol, resorcinol, hydroquinone, pyrogallol, hydroxyhydroquinone, phloroglucinol, other monocyclic polyhydroxy benzenes and dicyclic and polycyclic phenols such as naphthols and hydroxyanthracenes. Substitution products of the above mentioned phenols are also suitable, e.g. the corresponding halogenated, sulphonated and nitrated compounds and the corresponding ether derivatives. Examples of heterocyclic phenols include the hydroxy derivatives of heterocyclone, pyrrole, furan, thiophene, pyrazole, imidazole, oxazole, thiazole, triazole, tetrazole, pyridine, pyrimidine, pyrazine and triazine and the corresponding benzo-condensed derivatives.

In the synthesis of trans-diurethanes, two mol of alkali metal hydroxide or one mol of alkaline earth metal hydroxide are required for each mol of bis-N-chloramide. Stoichiometric quantities of hydroxide are preferably used in practice. If excess quantities of hydroxide are used, trans-cyclohexane-1,4-diamine is formed as by-product whereas, when less than equivalent quantities of hydroxide are used, the reaction does not proceed quantitatively and substantial quantities of acyl ureas are formed, among other by-products.

The process is carried out at temperatures of from 0° C. to 150° C., preferably 10° C. to 80° C. Diurethane formation proceeds exothermally.

The hydroxy compound is used in excess and may also serve as reaction medium. The minimum quantity required is that which will keep the mixture stirrable. It is therefore preferred to use saturated alkali metal hydroxide or alkaline earth metal hydroxide solutions in the alcohol or phenol used.

The process is preferably carried out by first preparing a solution of the hydroxide in the alcohol or phenol and then introducing the cyclohexane-1,4-dicarboxylic acid-bis-N-chloramide with stirring and cooling to temperatures below 10° C. The bis-N-chloramide generally dissolves within a few minutes with salt formation. A clear colorless solution is formed, from which a fine, white bulky precipitate separates gradually, more rapidly if the reaction mixture is heated to temperatures above 25° C. If desired, the reaction may be carried out in a suspension of the alkali metal or alkaline earth metal salt of cyclohexane-1,4-carboxylic acid-bis-N-chloramide. In that case, the salt dissolves during the reaction at the rate at which the diurethane forms and precipitates. Here again, the reaction is highly selective although at no point is a clear reaction solution obtained. The precipitate contains alkali metal chloride or alkaline earth metal chloride in the trans-diurethane. The reaction mixture may be worked up by, for example, the following method: In the case of trans-diurethanes which are difficult to dissolve in water, the precipitate is filtered off and the filtrate is concentrated by evaporation. The precipitate thereby obtained also consists of alkali metal or alkaline earth metal chloride and trans-diurethane. The precipitates are combined and digested with a small quantity of water, whereby the alkali metal chloride or alkaline earth metal chloride is dissolved away. In the case of trans-diurethanes which are less difficult to dissolve in water, the reaction mixture is evaporated to dryness and extracted with an organic solvent such as ethanol, ethyl acetate or chloroform, the alkali metal or alkaline earth metal chloride being left behind as residue. The liquid phase which contains the trans-diurethane, is then dried.

The trans-diurethanes mentioned above may be obtained highly pure and in almost quantitative yields by the process described here.

Preparation of the trans-diureas is carried out according to the invention by reacting the cyclohexane-1,4-dicarboxylic acid-bis-N-chloramide which has been obtained as described above with an amine in an aqueous medium in the presence of an alkali metal or alkaline earth metal hydroxide or alkali metal or alkaline earth metal oxide. The amines used may be primary or secondary, aliphatic or aromatic, mono-functional or polyfunctional amines. Examples of such amines include ammonia, methylamine, dimethylamine, ethylamine, diethylamine, ethylenediamine, isobutylamine, tertiary butylamine, aniline, ethanolamine, the isomeric cyclohexylamines, the isomeric phenylenediamines and substituted derivatives thereof, e.g., N-N'-diisopropylphenylenediamine and heterocyclic amines such as morpholine.

The reaction is carried out in water. The amine is used in excess, preferably in an excess of about 60 mol %. The reaction is carried out at temperatures of from 10° to 100° C., preferably at 25° to 70° C. The reaction time is generally from 2 to 5 hours.

The process is suitably carried out by suspending cyclohexane-1,4-dicarboxylic acid-bis-N-chloramide in water with vigorous stirring and adding the stoichiometric quantity of aqueous hydroxide dropwise at temperatures of from 0° to 5° C. with cooling. A clear solution of the alkali metal or alkaline earth metal salt of cyclohexane-1,4-dicarboxylic acid-bis-N-chloramide is thereby obtained. The amine is then added portion-wise and the reaction mixture is thereafter heated to a temperature of from 25° C. to 75° C. and kept at this temperature until the end of the reaction. After cooling, the precipitate of trans-diurea is filtered off, washed and dried. A second fraction of the trans-diurea may be recovered from the filtrate by first neutralizing the filtrate with a mineral acid, removing water, and then extracting with a suitable organic solvent, e.g. acetone or ethyl acetate.

The process disclosed in German Pat. No. 2,502,428 may be used to prepare trans-cyclohexane-1,4-disulphonyl-ureas. According to this process, cyclohexane-1,4-dicarboxylic acid-bis-N-chloramide is reacted with a sulphonic acid amide of the general formula R—SO$_2$—NH$_2$, in which R represents an amino group, a straight or branched chain, saturated or unsaturated aliphatic group having from 1 to 20 carbon atoms, a cycloaliphatic group having from 4 to 10 carbon atoms, a substituted or unsubstituted aromatic group or an alkyl aromatic or heterocyclic group, in a mixture of dimethyl formamide and water in the presence of excess alkali metal hydroxide at a temperature of from 10° C. to 50° C. Any primary sulphonamide may be used, both inoganic primary sulphonamides, e.g. sulphamide, and organic primary sulphonamides, for example aliphatic, cycloaliphatic and aromatic sulphonamides, and these may also be substituted. Suitable substituents are those which are inert towards isocyanates or react more slowly than sulphonamides, thus alkyl, nitro, halogen, sulpho, alkoxy, nitrilo, phosphonato, sulphamido and phenyl substituents are suitable. The following are examples of such organic sulphonamides: methane sulphonamide and its homologues containing from 2 to 20 carbon atoms, benzene sulphonamide, p-toluene sulphonamide, p-fluorobenzene sulphonamide, p-chlorobenzene sulphonamide, p-bromobenzene sulphonamide, p-iodobenzene sulphonamide, 2,4,5-trichlorobenzene sulphonamide, 3-sulphamidobenzene sulphoamide, 2-naphthyl sulphonamide and cyclohexyl sulphonamide.

The composition of the reaction medium to be employed depends on the solubility of the alkali metal hydroxide in the dimethyl formamide/water mixture, the solubility of the sulphonamide salt in dimethyl formamide and the basicity of the sulphonamide. The quantity of water should be sufficient to allow the alkali metal hydroxide to dissolve as far as possible completely in the reaction medium but, at the same time, it must not exceed a certain limit, beyond which the reaction does not stop at the formation of sulphonyl urea but proceeds to the acyl urea. This limit, which is specific to each sulphonamide, depends on the basicity of the sulphonamide and on its solubility. The quantity of dimethyl formamide should be sufficient to allow the sulphonamide salt to dissolve at least partly in the reaction medium. Suitable proportions can easily be determined by simple preliminary tests. Satisfactory results are achieved with a dimethyl formamide/water ratio of from 5:1 to 14:1.

For economic reasons, the alkali metal hydroxide used is preferably sodium hydroxide although the other alkali metal hydroxides are equally suitable. The alkali metal hydroxide should be used in at least the stoichiometric quantity. Four mol of alkali metal hydroxide are required for each mol of cyclohexane-1,4-dicarboxylic acid-bis-N-chloramide because it is only in its anionic form that the sulphonamide reacts as alkali metal salt in the required manner. In many cases it has been found advantageous to use an excess of alkali metal hydroxide. It is preferred to use an excess of up to 2 mol of alkali metal hydroxide per mol of cyclohexane-1,4-dicarboxylic acid-bis-N-chloramide.

Cyclohexane-1,4-dicarboxylic acid-bis-N-chloramide and the sulphonamide may be included in the process in stoichiometric quantities, i.e. in a molar ratio of 1:2, but the sulphonamide, which is generally the less expensive reactant, may suitably be added in an excess of up to 2 mol.

According to the invention, the trans-diureas prepared as described above may be converted into trans-cyclohexane-1,4-diisocyanate by treatment with gaseous hydrogen chloride in a solvent. Any of the above mentioned trans-diureas which have been prepared from a secondary amine may be used as starting materials. The reaction temperature employed is preferably within the range of from 80° C. to 200° C., more preferably 100° C. to 160° C. Gaseous hydrogen chloride is used either in the stoichiometric quantity or in excess. It may also be mixed with an inert gas such as carbon dioxide or nitrogen. The reaction times depend on the nature of the trans-diurea and are generally in the region of from 5 to 45 minutes. The nature of the solvent has no decisive influence on the course of the reaction. Suitable solvents include aromatic compounds such as benzene and toluene and chlorinated aromatic compounds such as monochlorobenzene, 1,2-dichlorobenzene and chloronaphthalene. The boiling point of the solvent should be higher than the reaction temperature employed in order that the reaction may be carried out at normal pressure, but excess pressure may be employed if desired.

Conversion of the trans-diurea may be carried out, for example, by dissolving or suspending it in a solvent, heating the resulting solution or suspension under reflux and then passing a stream of hydrogen chloride through it, optionally diluted with an inert gas.

After complete conversion of the trans-diurea, the supply of hydrogen chloride is stopped and any hydrogen chloride left in the reaction mixture is carefully driven off by means of an inert gas. The reaction mixture is then cooled, whereby the amine hydrochloride is in most cases precipitated quantitatively.

The method employed for working up the reaction mixture depends on the solubility of the amine hydrochloride formed as by-product. If this is precipitated almost quantitatively from the cooled reaction mixture, it is removed by filtration or centrifuging. The solvent is then evaporated off and the residue, containing trans-cyclohexane-1,4-diisocyanate, is subjected to fractional distillation. If the amine hydrochloride is partly soluble in the cooled reaction mixture, the solvent is first distilled off and the diisocyanate is then separated by solvent extraction with an alkane and finally subjected to fractional distillation. The amine can be recovered quantitatively from an aqueous solution by reaction of the hydrochloride with an alkali metal hydroxide followed by extraction, and may then be used again for the preparation of the trans-diurea.

Another possible method of preparing trans-cyclohexane-1,4-diisocyanate comprises thermal decomposition of the trans-cyclo-hexane-1,4-diurethanes obtained by the process according to the invention. Suitable methods are disclosed in German Offenlegungsschrift No. 2,410,505, British Pat. No. 1,247,451 and U.S. Pat. No. 3,962,302. In the process described in German Offenlegungsschrift No. 2,410,505, the urethane is introduced into a non-catalytic zone of pyrolysis which is maintained at a reaction temperature of from 350° C. to 550° C. and a pressure of less than 1 bar, the reaction products are removed from the reaction zone in the vapor phase after a dwell time therein of less than about 15 seconds, and the reaction products which are in the vapor phase are cooled to condense cyclohexane-1,4-diisocyanate, the alcohol formed as by-product being left in the vapor phase. In the process described in British Pat. No. 1,247,451, the diurethane is heated to a temperature of from 400° C. to 600° C. in the presence of from 0.5% to 3% by weight of a Lewis acid, e.g., iron chloride or aluminum chloride, and the vapor mixture is then condensed to separate the diisocyanate. In the process according to U.S. Pat. No. 3,962,302, thermal decomposition of the urethane is carried out in an organic solvent, e.g., an aliphatic, cycloaliphatic or aromatic hydrocarbon, at 175° to 350° C.

Trans-cyclohexano-1,4-diisocyanate may also be prepared by degradation of the corresponding disulphonyl ureas. See, in this connection, the process by H. Ulrich et al., Angew. Chem. 78 (1966), pages 746 to 747. For example, the reaction may be carried out at temperatures of from 100° to 230° C. in an inert high boiling solvent such as nitrobenzene, ortho-dichlorobenzene, 1,2,4-trichlorobenzene or 2-chloronaphthalene.

The process according to the invention provides a stereo-specific synthesis which, starting from a cis-trans mixture of cyclohexane-1,4-dicarboxylic acid or one of its monomeric, oligomeric or polymeric esters, leads to numerous pure trans compounds in almost quantitative yield via the stage of a special modification of the cyclohexane-1,4-dicarboxylic acid diamide and a special modification of the cyclohexane-1,4-dicarboxylic acid-bis-N-chloramide by a Hofmann rearrangement.

The process is superior to the known processes for the production of such compounds in that it uses inexpensive starting materials, i.e., cyclohexane-1,4-dicarboxylic acid or its esters, which in part are available as raw materials or waste products or polyester production, and leads to the desired trans compound in high yields by simple, smooth reactions which require simple apparatus. The main advantage of the process according to the invention is that it is based on a stereo-specific synthesis. Whereas, in the known processes, the trans component can only be separated from the original cis-trans isomeric mixture of the starting materials and worked up, the process provided by the present invention for the first time provides for complete conversion of the cis-trans mixture of the starting materials into the desired pure trans-reaction products, regardless of the proportion of cis-compound to trans-compound in the starting materials.

The products obtainable by the process according to the invention are valuable intermediate compounds. Trans-cyclohexane-1,4-diamine, for example, may be reacted with dicarboxylic acid chlorides to produce polyamides which are distinctly superior in their physical properties such as tear resistance, shrink resistance, non-fusibility and other use properties to those products which have been produced from a cis-trans isomeric mixture of cyclohexane-1,4-diamine. The reaction of trans-cyclohexane-1,4-diamine with terephthaloyl chloride, for example, results in a polyamide which can be spun from an anisotropic solution in concentrated sulphuric acid to produce fibers with high temperature resistance and high modulus. Polyurethanes obtained from trans-cyclohexane-1,4-diisocyanate are distinguished by high elongation on tearing, high tension characteristics, low permanent elongation, high restoring forces and absence of hysteresis losses. The properties of polymers produced from the pure trans-starting materials are in all cases more valuable than the properties of polymers produced from the corresponding mixtures of cis- and trans-isomers.

The trans-cyclohexane-1,4-diisocyanate may be used for making plyurethane elastomers, coatings and the like. The coatings have improved light stability over coatings prepared from arylene diisocyanates. The process provided by the invention is described in more detail in the Examples given below. All the compounds were identified by their IR, NMR, UV and mass spectra. Any diureas, diurethanes or disulphonyl ureas which have not yet been described in the literature were also prepared by addition reactions with trans-cyclohexane-1,4-diisocyanate and their identity was confirmed by comparisons.

Examples 1 to 5 relate to the preparation of cyclohexane-1,4-dicarboxylic acid diamide by ammonolysis of an alkyl ester and glycol ester and of an oligomeric ester of cyclohexane-1,4-dicarboxylic acid.

EXAMPLE 1

In a 1 liter glass autoclave equipped with glass inlet tube, stirrer and reflux condenser, 163.7 g (0.8185 mol) of cyclohexane-1,4-dicarboxylic acid dimethyl ester (cis/trans ratio=9:1) were added rapidly to 564 g of ethylene glycol (solvent and reactant) ($\sim$9.1 mol) and the reaction mixture was then saturated with ammonia at room temperature. The mixture was then slowly heated. The methanol formed in the reaction began to distill off at 80° C. When the temperature was raised to between 100° C. and 130° C. with the simultaneous introduction of ammonia, trans esterification was completed and the methanol formed was distilled off. At the end of the reaction, a homogeneous solution was obtained from the two phases originally present. Heating was than continued for an additional 15 minutes under reflux while a slow stream of ammonia was passed through the hot solution.

When trans esterification had been completed, the reflux condenser was disconnected and amidation of the reaction mixture was completed at an ammonia pressure of 5 to 9 bar and a temperature of from 110° C. to 135° C. A fine, white crystalline precipitate separated from the initially clear solution. In the course of 5 hours, this precipitate grows to form a thick crystalline paste. The reaction is then complete. After release of pressure in the autoclave, the white precipitate was suction filtered to remove the glycollic mother liquor and washed three times with cold water. 115.1 g (0.675 mol) amounting to 82% of the theoretical yield, of pure cyclohexane-1,4-dicarboxylic acid diamide, having a melting point of 345° C. to 350° C., was obtained after drying. 14.0 g, amounting to 10% of the theoretical yield of cyclohexane-1,4-dicarboxylic acid diamide were found in the glycollic filtrate and an additional 9.15 g, amounting to 7% of the theoretical yield, in the wash water. The actual yield of diamide is thus 99% of the theoretical yield.

The mother liquor, together with the cyclohexane-1,4-dicarboxylic acid diamide dissolved in it, was used again for the next batch without any further treatment, i.e. it was reacted with the cis/trans mixture of cyclohexane-1,4-dicarboxylic acid dimethyl ester. The yield of cyclohexane-1,4-dicarboxylic acid diamide which was obtained directly by filtration from the glycollic medium was thus raised to 95–97% of the theoretical yield.

EXAMPLE 2

By a method similar to that of Example 1, 163.7 g of cyclohexane-1,4-dicarboxylic acid dimethyl ester (cis/trans ratio=1:1) were mixed with 564 g of ethylene glycol in a 1 liter glass autoclave and then heated to 80° to 110° C., reacted in the presence of ammonia as catalyst and finally completely decomposed into the cyclohexane-1,4-dicarboxylic acid diamide by heating to 110° C. to 135° C. under an ammonia pressure of 5 to 9 bar. 119.2 g (0.7 mol) equivalent to 85.5% of the theoretical yield, of cyclohexane-1,4-dicarboxylic acid diamide could be directly obtained after cooling to room temperature, filtration of the glycollic mother liquor and washing of the residue with ice water.

EXAMPLE 3

By a method similar to that of Example 1, 163.7 g of cyclohexane-1,4-dicarboxylic acid dimethyl ester (cis/trans ratio=1:9) were trans esterified with 564 g of ethylene glycol and then decomposed into cyclohexane-1,4-dicarboxylic acid diamide by heating to temperatures of from 110° C. to 140° C. at an ammonia pressure of 5 to 10 bar. 129.0 g (0.758 mol), equivalent to 92.6% of the theoretical yield of cyclohexane-1,4-dicarboxylic acid diamide were obtained from the glycollic reaction mixture after filtration and repeated washing with water at 15° C. A further 9.0 g=6.47% of cyclohexane-1,4-dicarboxylic acid diamide were dissolved in the glycollic filtrate and 1.84 g=1.32% were dissolved in water.

EXAMPLE 4

224 g (1.30 mol) of cyclohexane-1,4-dicarboxylic acid (cis/trans mixture 7:3) and 1,000 g of ethylene glycol were heated under reflux for 1 hour at 190° C. to 195° C. with stirring in the presence of 0.5% by weight of antimony trioxide, based on the quantity of cyclohexane-1,4-dicarboxylic acid. 600 g of ethylene glycol/water (about 47 g water of reaction) were subsequently distilled off at normal pressure over a period of 5 hours. The oily residue, an oligomeric mixture in excess ethylene glycol, was transferred to the autoclave described in Example 1 and treated with ammonia as also described in that Example. The reaction temperature was 120° C., the ammonia pressure 9 bar and the reaction time 10 hours. The autoclave pressure was then released and the contents cooled to room temperature. 250 ml of water were added to the reaction suspension which contained about 400 g of glycol. The reaction mixture was then filtered and washed, first with 200 ml of water and then with 100 ml of methanol. 195 g, equivalent to 87.2% of the theoretical yield, of cyclohexane-1,4-dicarboxylic acid diamide in the purest form were left after drying. A further quantity of cyclohexane-1,4-dicarboxylic acid diamide amounting to 10% of the theoretical yield, was found to be dissolved in the mother liquor.

EXAMPLE 5

224 g (1.30 mol) of cyclohexane-1,4-dicarboxylic acid (cis/trans=3:2) and 1,500 g (24.2 mol) of ethylene glycol were heated under reflux in a 2 liter glass autoclave for 45 minutes with stirring. 750 g of glycol/water were subsequently distilled off at normal pressure over a period of 5 hours. Esterification was by then completed (determination of acid number) and, when the autoclave contents had cooled to 130° C., ammonia was introduced at a pressure of 6 bar for 3 hours and the contents at the same time thoroughly mixed. The autoclave was then cooled and released to normal pressure and the reaction suspension was filtered. The filter residue, moist with glycol, was then washed twice, each time with 100 ml portions of methanol or water, respectively, and then dried under vacuum at 60° C. to 80° C. The yield of pure cyclohexane-1,4-dicarboxylic acid diamide was 187 g, equivalent to 83.6% of the theoretical yield.

After removal of the methanol and water, the glycolic filtrate was circulated together with the wash waters, i.e. it was reacted with fresh cyclohexane-1,4-dicarboxylic acid as described above. The yield of solid cyclohexane-1, 4-dicarboxylic acid diamide was thereby increased to 89% of the theoretical yield after the second cycle and to 93.5% of the theoretical yield after the third cycle.

The following Examples 6 and 7 relate to the chlorination of the diamide to bis-N-chloramide in aqueous or hydrochloric acid suspension.

EXAMPLE 6

172 g (1.01 mol) of cyclohexane-1,4-dicarboxylic acid diamide prepared according to one of the Examples 1 to 4 (filter residue) were dispersed in 2 liters of 17% hydrochloric acid at 5° C. with vigorous stirring and a powerful stream of chlorine was then passed through this suspension for 30 minutes. The reaction temperature should not exceed 10° C. during this operation. The mixture was stirred very vigorously to ensure efficient mass transfer. Chlorination was completed after 90 minutes and the cyclohexane-1,4-bis-N-chloramide was separated from the suspension by filtration through a glass frit and washed 3 times with 100 ml portions of cold water (5°–10° C.). The yield was 225 g (0.942 mol)=93% of the theoretical yield. Cyclohexane-1,4-dicarboxylic acid-bis-N-chloramide was obtained in the form of pure white crystals, which were then dried at 40° C. The percentage of active chlorine determined by titration was found to be 99.5% of the theoretical amount.

EXAMPLE 7

17.2 g of cyclohexane-1,4-dicarboxylic acid diamide (0.101 mol) prepared according to Example 5 (filter residue) were suspended in 130 ml of water in a glass autoclave and then reacted under conditions of vigorous stirring for 15 minutes under a chlorine pressure of 5 to 8 bar at 5° to 15° C. The pressure was then released and the precipitate filtered off and washed free from chlorine with ice water. 22.0 g (0.092 mol)=91% of the theoretical yield of cyclohexane-1,4-dicarboxylic acid-bis-N-chloramide were obtained. The active chlorine content determined by titration was found to be 99.2% of the theoretical amount.

The following Example 8 relates to the preparation of trans-cyclohexane-1,4-diamine.

EXAMPLE 8

In a 250 ml 3-necked flask, 9.57 g (0.04 mol) of cyclohexane-1,4-dicarboxylic acid-bis-N-chloramide were dispersed in 70 ml of water with vigorous stirring, and a solution of 10.4 g (0.26 mol) of sodium hydroxide in 100 ml of water was added dropwise at 5° C. The reaction temperature should not exceed 8° C. When all the sodium hydroxide solution had been added, a clear solution was obtained (formation of N-chloramide sodium salt). The external cooling means were then removed and replaced by a water bath at 35° C. When the reaction temperature reached 27° C., a vigorous exothermic reaction took place so that the temperature of the reaction mixture rose to 66° C. After a further 4 minutes, the reaction temperature began to fall. The mixture was then reheated at 50°–75° C. for 45 minutes. A clear, light brown solution was finally obtained. This was extracted with chloroform for 3.5 hours in a liquid-liquid extractor. 4.273 g (37.42 mMol)=93.5% of the theoretical yield of pure trans-cyclohexane-1,4-diamine was obtained from the chloroform phase after dehydration over calcium chloride and removal of the solvent. The diamine was obtained in the form of colorless needles (melting point 53°–60° C.). It was identified by analysis of the elements, the IR, NMR and mass spectra and by titration (perchloric acid/acetic acid=99.18%).

The following Examples 9 to 12 relate to the preparation of trans-diurethanes.

EXAMPLE 9

In a 2 liter 3-necked flask equipped with a KPG stirrer, reflux condenser and dropping funnel, 41.16 g (1.03 mol) of finely powdered sodium hydroxide were first dissolved in 1.2 liters of methanol with vigorous stirring. The reaction temperature rose to 40° C. The contents were then cooled to 5° C. and 123.0 g (0.5145 mol) of cyclohexane-1,4-dicarboxylic acid-bis-N-chloramide (prepared according to Example 6) were added portionwise over a period of 1 hour at such a rate that the temperature in the reaction vessel did not rise above 10°

C. When all 123.0 g had been added, a clear solution (sodium salt of cyclohexane-1,4-dicarboxylic acid-bis-N-chloramide) was obtained. The cooling bath was then removed and the Hofmann reaction started by heating to 24° C. The temperature inside the flask rose to 45° C. due to the heat of reaction liberated. Shortly after onset of the Hofmann rearrangement, the clear solution became cloudy due to precipitation of sodium chloride. Most of the reactant had undergone reaction after 15 minutes, as could be detected by a fall in the reaction temperature to 35° C.

The mixture was then heated to 45° C. for 90 minutes and finally refluxed for 1 hour to complete the reaction. It was then cooled to room temperature and the trans-dimethyl-1,4-cyclohexane-dicarbamate was filtered off together with the precipitated sodium chloride. The filter residue was washed free from chloride with water, and 98.8 g (0.43 mol), equivalent to 83.5% of the theoretical yield, of pure trans-dimethyl-1,4-cyclohexane dicarbamate (melting point 265° to 267° C.) remained behind. A further 9.6 g, equivalent to 7.2%, of the theoretical yield of trans-dimethyl-1,4-cyclohexane dicarbamate were contained in the methanollic filtrate and the wash water.

EXAMPLE 10

By a method similar to that of Example 9, 16 g (0.4 mol) of finely powdered sodium hydroxide were dissolved in 250 ml of ethanol with vigorous stirring, and 47.8 g (0.2 mol) of cyclohexane-1,4-dicarboxylic acid-bis-N-chloramide, synthesized according to Example 6 were added portion-wise at 0°–5° C. The clear solution was then heated to 28° C., at which point Hofmann rearrangement set in and the reaction temperature rose to 52° C. After the reaction had died down, the mixture was vigorously stirred for 1 hour at 60° C. and then under reflux for 15 minutes. After cooling to 10° C., the reaction mixture (sodium chloride and trans-diethyl-1,4-cyclohexane dicarbamate) was separated by filtration and the urethane was freed from sodium chloride impurities by washing with water. The yield of pure trans-diethyl-1,4-cyclohexane dicarbamate (melting point 245° to 248° C.) was 48.6 g (0.188 mol), equivalent to 94% of the theoretical yield.

EXAMPLE 11

191.2 g (0.8 mol) of cyclohexane-1,4-dicarboxylic acid-bis-N-chloramide (prepared according to Example 6) were added portion-wise to a solution of 64 g (1.6 mol) of sodium hydroxide in 2 liters of ethylene glycol with vigorous stirring at 10° C. with external cooling. When all the chloramide had gone into solution, the cooling means were removed and the reaction mixture was heated to 40° C. Hofmann rearrangement set in and the reaction temperature rose to 62° C. The reaction mixture was then heated to 60° C. for 30 minutes to complete the reaction and then stirred at room temperature for 10 hours. The trans-di-(2-hydroxyethyl)-1,4-cyclohexane dicarbamate formed in the reaction, together with sodium chloride adhering to it, was separated from the glycollic mother liquor by filtration. Residues of ethylene glycol and sodium chloride still adhering to it were then removed by suspending the reaction product three times in 50 cc portions of ice water. 128.5 g (0.4426 mol), equivalent to 55% of the theoretical yield, of pure trans-di-(2-hydroxyethyl)-1,4-cyclohexane dicarbamate, melting point 197° C. to 199° C., were obtained in this way. A further 98.2 g (0.338 mol), equivalent to 42% of the theoretical amount, of trans-di-(2-hydroxyethyl)-1,4-cyclohexane dicarbamate were obtained from the mother liquor and the wash water by removing all of the solvent under vacuum and separating the diglycol urethane from the sodium chloride which had been precipitated with it by extraction with cold ethanol.

EXAMPLE 12

Similarly to Example 11, 179.5 g (0.75 mol) of cyclohexane-1,4-dicarboxylic acid-bis-N-chloramide were added portion-wise with vigorous stirring to a solution of 60 g (1.5 mol) of sodium hydroxide in 2 liters of butane-1,4-diol at 10° C. and Hofmann rearrangement was then carried out at 30°–40° C. After a reaction time of 5 hours, the reaction mixture was no longer oxidizing, and part of the trans-di-(4-hydroxybutyl)-1,4-cyclohexane-dicarbamate formed in the reaction had been precipitated together with sodium chloride. After filtration and removal of the adhering sodium chloride by washing with water, 120 g (0.3465 mol)=46.2% of the theoretical yield of pure trans-di-(4-hydroxybutyl)-1,4-cyclohexane dicarbamate (Mp 170° to 175° C.) were obtained in the form of fine white needles. A further 98.3 g (0.284 mol), equivalent to 37.9% of the theoretical amount, of trans-1,4-diurethane were obtained from the mother liquor after removal of the solvent and extraction of the residual salt with cold ethanol.

The following Examples 13 to 19 relate to the preparation of trans-diureas.

EXAMPLE 13

182 g (0.76 mol) of 1,4-cyclohexane-bis-N-chloramide, prepared according to Example 6, were suspended in 750 cc of water with vigorous stirring, and 60.8 g (1.52 mol) of sodium hydroxide dissolved in 300 ml of water were added dropwise at temperature between 0° to 5° C. 200 ml of diethylamine (1.9 mol) were then added drop-wise to the clear solution (sodium salt of cyclohexane-1,4-dicarboxylic acid-bis-N-chloramide) over a period of 10 minutes. The reaction mixture was then heated to 40° C. for 60 minutes and then for a further 45 minutes to 55° C. to complete the reaction. A fine sludge of trans-(1,4-di-(N',N'-diethyl-ureido)-cyclohexane then formed. This was isolated by filtration through a glass frit and washed 5 times with 250 ml portions of water. After drying, 175.7 g (0.562 mol), equivalent to 74% of the theoretical yield, of pure trans-1,4-di-(N',N'-diethyl-ureido)-cyclohexane were obtained in the form of colorless needles, melting point 225° C. to 228° C. The filtrate was then neutralized with dilute hydrochloric acid, evaporated to dryness and extracted with acetone. A further 54.6 g (0.174 mol), equivalent to 23% of the theoretical yield, of the pure trans-urea were thereby obtained. The total yield of pure trans-1,4-di-(N',N'-diethyl-ureido)-cyclohexane was therefore 97% of the theoretical yield.

EXAMPLE 14

47.9 g (0.2 mol) of cyclohexane-1,4-dicarboxylic acid-bis-N-chloramide (obtained according to Example 6) were added portion-wise to 500 ml of concentrated ammonia at 0° C. with vigorous stirring, care being taken to insure that the reaction temperature did not exceed 5° C. A clear solution formed shortly after all the chloramide had been introduced into the reaction solution. The cooling bath was then removed and the reaction mixture heated to 30° to 35° C. A fine crystalline precipitate soon began to form. The reaction mixture was stirred for a further 3 hours at 40° C. to complete the reaction. The mixture was then no longer oxidizing. The trans-1,4-diureido-cyclohexane formed in the reaction was isolated by filtration. It was washed twice, each time with 75 ml of ice water, to remove ammonium chloride adhering to it as impurity. After drying, 34.8 g (0.174 mol), equivalent to 87% of the theoretical yield, of trans-1,4-diureido-cyclohexane (Mp>320° C.) were obtained in the form of colorless needles. An additional portion of the urea was still present in the ammoniacal filtrate, from which it could be recovered by extraction with ethyl acetate after evaporation of the water.

EXAMPLE 15

Similarly to Example 13, 182 g (0.76 mol) of cyclohexane-1,4-dicarboxylic acid-bis-N-chloramide were suspended in 700 ml of water with vigorous stirring, and 60 g (1.5 mol) of sodium hydroxide dissolved in 250 ml of water were added drop-wise at 0°–5° C. After a clear solution had formed and cooled to 0° C., 128 g (2.1 mol) of ethanolamine were added. The temperature should not exceed 5° C. throughout the addition of ethanolamine. The clear solution was then heated to room temperature, at which point Hofmann rarrangement set in and a fine white precipitate formed at 33° C. The reaction mixture was then vigorously stirred for one hour at 50° C. to complete the reaction, and the urea formed was isolated by filtration and freed from the sodium chloride adhering to it by washing with ice water. 177.5 g (0.616 mol), equivalent to 81% of the theoretical yield, of trans-1,4-di-(N'-2-hydroxyethyl ureido)-cyclohexane could be obtained after drying.

EXAMPLE 16

47.9 g (0.2 mol) of cyclohexane-1,4-dicarboxylic acid-bis-N-chloramide, prepared according to Example 7, were vigorously stirred up in 250 ml of water to form a fine suspension, and 16 g (0.4 mol) of sodium hydroxide dissolved in 75 ml of water were added at 0° C. 43.56 g (0.5 mol) of morpholine were added dropwise to this solution. Hofmann rearrangement and working up of the reaction product were carried out analogously to Example 1. 46.25 g (0.136 mol), equivalent to 67.9% of the theoretical yield, of pure trans-cyclohexane-1,4-bis-morpholine-urea were obtained from the reaction mixture in the form of a white powder (Mp>320° C.) by filtration. A further 12.8 g equivalent to 19% of the theoretical yield of the urea were isolated from the mother liquor by extraction with ethyl acetate after evaporation.

EXAMPLE 17

Similarly to Example 13, 24 g (0.1 mol) of cyclohexane-1,4-dicarboxylic acid-bis-N-chloramide (synthesized according to Example 6) were suspended in 100 ml of water at 0° C., and 8.4 g (0.21 mol) of sodium hydroxide dissolved in 25 ml of water were added. When salt formation had been completed, 20 g of cyclohexylamine (0.2016 mol) were added with further cooling and the Hofmann rearrangement was then carried out. 26.7 g (0.073 mol), equivalent to 73% of the theoretical yield, of pure trans-1,4-di-(N'-cyclohexylureido)-cyclohexane were obtained by filtration. This substance precipitates in the form of white needles which begin to decompose slowly at 300° C.

EXAMPLE 18

Similarly to Example 13, 119.6 g (0.5 mol) of cyclohexane-1,4-dicarboxylic acid-bis-N-chloramide (prepared according to Example 7) were dispersed in 750 ml of water at 0° C., and 46 g of sodium hydroxide (1.15 mol) dissolved in 120 ml of water were added dropwise. 80 g of tertiary butylamine (1.1 mol) were subsequently added. Hofmann rearrangement and isolation of the urea were carried out similarly to Examples 13 to 17. The yield of pure trans-1,4-di-(N'-tertiary butyl-ureido)-cyclohexane (colorless crystals, decomposition point >300° C.) was 118 g (0.3776 mol), equivalent to 75% of the theoretical yield.

EXAMPLE 19

Similarly to Example 13, 36 g (0.9 mol) of sodium hydroxide dissolved in 250 ml of water were added at a low temperature to 100 g (0.418 mol) of cyclohexane-1,4-dicarboxylic acid-bis-N-chloramide, prepared according to Example 6, and, when salt formation had been completed, 200 g (1.04 mol) of N,N'-diisopropyl-p-phenylene diamine were added. Hofmann rearrangement and separation of the urea formed in the reaction were carried out as described in Examples 12 to 17. 187 g (y0.34 mol), equivalent to 81% of the theoretical yield, of pure trans-1,4-di-(N'-isobutyl-N'-p-isobutylaminophenyl-ureido)-cyclohexane were obtained by filtration as a beige colored powder having a decomposition point at 245° to 247° C.

The following Example relates to the preparation of a trans-cyclohexane-1,4-disulphonyl urea.

EXAMPLE 20

32 g (0.80 mol) of sodium hydroxide were dissolved in 40 g of water. 400 ml of dimethyl formamide were added at 25° C. 68.5 g (0.40 mol) of finely powdered p-toluene sulphonamide were added portion-wise to this solution at room temperature with vigorous stirring. The sodium salt of the tosylamide was thereby formed, which precipitated as fine, white crystals. The suspension was then cooled to 5° C. and a slurry of 47.6 g (0.20 mol) of cyclohexane-1,4-dicarboxylic acid-bis-N-chloramide in 100 ml of dimethyl formamide was added with vigorous stirring. The heat of reaction (formation of the sodium salt of bis-N-chloramide) was removed by cooling (reaction temperature >15° C.). When all the N-chloramide had been introduced into the reaction mixture, the mixture was heated to 25° C. An exothermic reaction then took place and the reaction temperature rose to 48° C. The suspension was highly fluid, and a white precipitate was formed after about 5 minutes. The reaction mixture was heated to 50° C. for 55 minutes to complete the reaction. It was then diluted with 1 liter of water and freed from undissolved constituents. The filtrate was then acidified to pH=2 with dilute mineral acid. A colorless, bulky precipitate formed, which was dried in a vacuum drying oven at 80° C. after it had been washed free from chlorine. The yield of trans-1,4-cyclohexyl-bis-(p-tolyl-sulphonyl urea) was 64.2 g (0.25 mol), equivalent to 62.4% of the theoretical yield. (Mp >350° C.).

Examples 21 to 25 relate to the preparation of trans-cyclohexane-1,4-diisocyanate.

EXAMPLE 21

19.16 g (0.08 mol) of cyclohexane-1,4-dicarboxylic acid-bis-N-chloramide (synthesized as in Example 7)

were finely divided in 75 ml of water at 0° C. with vigorous stirring. 6.4 g (1.16 mol) of sodium hydroxide dissolved in 75 ml of water were then added dropwise at such a rate that the temperature in the reaction vessel did not rise above 5° C. A clear solution formed when all of the sodium hydroxide had been added. 20 g (0.177 mol) of a 40% by weight aqueous dimethylamine solution was added dropwise with cooling and the reaction mixture was then heated. The solution became cloudy at 25° C. and the temperature of the reaction mixture rose to 46° C. and at the same time the quantity of precipitate increased. The reaction mixture was stirred for 2 hours at 50° C. to complete the reaction. At the end of that time, it was no longer oxidizing. The alkaline solution was then adjusted to pH 6 with dilute hydrochloric acid and the whole suspension was then pumped through a tube into 250 ml of o-dichlorobenzene which had been heated to 110° C. The water distilled off at the top and a beige colored, salt like mass precipitated in the o-dichlorobenzene. Finally, 30 ml of o-dichlorobenzene were distilled off under vacuum at 110° C. to remove the last traces of water. The suspension of substituted urea, sodium chloride and dimethylamine hydrochloride left behind was heated to 150° C. to 155° C. and saturated with HCl gas in the course of 30 minutes. It was then cooled to 100° to 110° C. and the hydrogen chloride dissolved in it was removed by careful stripping with a stream of nitrogen over a period of 1 hour. The residue was then cooled to 10° C. and the diisocyanate formed was filtered from sodium chloride and dimethylamine hydrochloride. The filter residue was washed 3 times with 25 ml portions of o-dichlorobenzene and the combine filtrates were fractionally distilled. 10.67 g (0.064 mol), equivalent to 80% of the theoretical yield, of pure trans-cyclohexane-1,4-diisocyanate (Mp 62° to 64° C.), distilled over at 117° C. to 120° C./10 to 13 torr.

EXAMPLE 22

In a 1 liter glass autoclave, 161 g (0.517 mol) of trans-1,4-di-(N',N'-diethylureido)-cyclohexane (prepared as in Example 13) were suspended in 700 ml of chlorobenzene and heated to 150° C. HCl gas was then forced in at a pressure of 6 bar with vigorous stirring. After 45 minutes, the autoclave was cooled to 80° C. to 100° C. and the pressure released.. Most of the diethylamine hydrochloride produced in the reaction was obtained in the form of colorless, shiny platelets. The reaction mixture was carefully stripped with an inert gas (nitrogen, carbon dioxide) for an additional 30 minutes to remove any dissolved HCl gas and decompose any carbamoyl chloride formed, and the mixture was then cooled to 10° C. and filtered to remove diethylamine hydrochloride. The filter residue was washed twice with 250 ml portions of chlorobenzene. 77.3 g (0.465 mol), equivalent to 90% of the theoretical yield, of pure trans-cyclohexane-1,4-diisocyanate (Mp 63° to 64° C.) precipitated in the for of colorless scales from the combined chlorobenzene filtrates after fractional distillation.

EXAMPLE 23

A mixture of 50 g (0.218 mol) of trans-dimethyl-1,4-cyclohexane dicarbamate (synthesized according to Example 9) was heated to 220° C. in 300 ml of n-hexadecane and kept at this temperature for 3 hours. At the same time, a stream of nitrogen was passed through the reaction mixture at the rate of 15 liters per hour. The methanol formed in the reaction distilled off at the top of a condenser which was maintained at 80° C. After the reaction had been completed, the reaction mixture was cooled to 10° C. and filtered to remove unreacted diurethane, monoisocyanate and a certain quantity of polymeric constituents. 63.7% of trans-cyclohexane-1,4-diisocyanate (MP 60°-63° C.) were obtained from the filtrate. EXAMPLE 24

48.5 g (0.188 mol) of trans-diethyl-1,4-cyclohexanedicarbamate (synthesized according to Example 10) were heated to 420° C. in an evaporator and passed over a 25 meter long bed of Raschig rings (temperature 450° C.) together with a stream of nitrogen (25 liters per hour), and the vapors liberated were rapidly chilled to 100° C. Trans-cyclohexane-1,4-diisocyanate (52.2% of the theoretical yield) formed in the process was separated from ethanol (89.7% of the theoretical amount) by fractional condensation before those two components could recombine to form the urethane.

EXAMPLE 25

64.2 g (0.25 mol) of trans-1,4-cyclohexane-bis-(p-tolyl-sulphonyl-urea) prepared as in Example 20 were reacted in 350 ml of nitrobenzene in a 1 liter glass autoclave at 230°-250° C. for 2 hours with stirring. The pressure was then released from the resulting clear solution and the nitrobenzene used as solvent was distilled off under vacuum. 20.7 g (0.124 mol), equivalent to 49.7% of the theoretical yield, of pure trans-1,4-cyclohexane diisocyanate were obtained from the solid, salt-like residue by extraction with hot hexane. The residue consisted of a mixture of p-toluene sulphonamide, the sulphonyl urea originally put into the process, monoisocyanate and polymeric acyl urea.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a trans-cyclohexane-1,4-diisocyanate which comprises (a) reacting ammonia with cyclohexane-1,4-dicarboxylic acid, or a lower alkyl ester, a glycol ester, an oligomeric ester or a polyester thereof or a mixture of such compounds at an ammonia partial pressure of from 0.1 to 50 bar in a polyhydric alcohol at a temperature of from about 25° C. to about 200° C., (b) separating the resulting solid dicarboxylic acid diamide precipitated under these conditions from the reaction mixture, (c) freeing the solid diamide from water soluble constituents adhering thereto, (d) suspending the resulting solid diamide in an aqueous mineral acid or in water, (e) chlorinating the diamide at a temperature of from 0° C. to 40° C. to form cyclohexane-1,4-dicarboxylic acid-bis-N-chloramide, (f) reacting the chloramide with a monohydric alcohol, a polyhydric alcohol, or a carbocyclic or heterocyclic phenol which is capable of at least partly dissolving an alkali metal or alkaline earth metal hydroxide in the presence of said alkali metal or alkaline earth metal hydroxide to form trans-cyclohexane-1,4-diurethane, and (g) heating said trans-cyclohexane-1,4-diurethane to form trans-cyclohexane-1,4-diisocyanate.

* * * * *